United States Patent [19]

Bartmann et al.

[11] 4,296,121
[45] Oct. 20, 1981

[54] NOVEL PROSTAGLANDIN DERIVATIVES OF THE Δ2-PGF$_2$ AND Δ2-PGE$_2$ SERIES AND PROCESS FOR THEIR MANUFACTURE

[75] Inventors: Wilhelm Bartmann, Bad Soden am Taunus; Gerhard Beck, Frankfurt am Main; Ulrich Lerch, Hofheim am Taunus; Elmar Konz, Bad Soden am Taunus, all of Fed. Rep. of Germany

[73] Assignee: Hoechst Aktiengesellschaft, Frankfurt am Main, Fed. Rep. of Germany

[21] Appl. No.: 62,937

[22] Filed: Aug. 2, 1979

[30] Foreign Application Priority Data

Aug. 4, 1978 [DE] Fed. Rep. of Germany ....... 2834248

[51] Int. Cl.$^3$ ................ C07D 333/24; A61K 31/557; C07D 307/54; C07C 177/00
[52] U.S. Cl. .................................. 424/275; 424/276; 424/285; 424/305; 424/317; 542/426; 542/429; 560/121; 560/118; 562/503; 562/500
[58] Field of Search ....................... 560/121; 562/503; 424/305, 317, 275, 276, 285; 542/426, 429

[56] References Cited

U.S. PATENT DOCUMENTS 4,124,601 11/1978 Smith .......................... 260/346.22
4,131,738 12/1978 Smith ............................. 560/121
4,215,142 7/1980 Hayashi et al. .................. 424/305

Primary Examiner—Robert Gerstl
Attorney, Agent, or Firm—Curtis, Morris & Safford

[57] ABSTRACT

What is disclosed are compounds of the formula

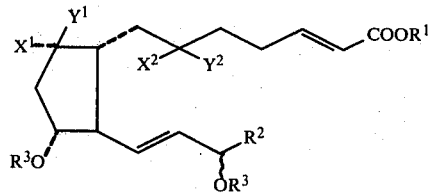

which are structurally related to natural prostaglandins and a process for their manufacture. The compounds have valuable pharamacological properties and, therefore, they can be used as medicaments.

7 Claims, No Drawings

NOVEL PROSTAGLANDIN DERIVATIVES OF THE Δ2-PGF₂ AND Δ2-PGE₂ SERIES AND PROCESS FOR THEIR MANUFACTURE

Prostaglandins are a group of fatty acids which occur in numerous tissues and organs of man and animals. The basic skeleton of natural prostaglandins consists of 20 carbon atoms arranged in the form of a five-membered ring with two adjacent linear side chains.

The prostaglandins have pharmacological effects, inter alia, in the field of reproduction, on the bronchial myogenic tonus, on the blood pressure and in gastroenterology. The pharmacological properties of natural prostaglandins are the subject of numerous publications, for example by N. H. Andersen and P. W. Ramwell in Arch. Internal Med. 133, 30 (1974); R. L. Jones in Pathobiology Ann. 1972, 359; J. Pike in Scient. American 225, 84 (1971) or M. P. L. Caton in Progress in Med. Chem. volume 8, ed: Butterworth, London 1971.

The synthesis of analogs of prostanoic acids which do not occur in nature and in which the numerous pharmacological properties of natural prostaglandins are differentiated increases in importance.

The present invention provides novel compounds of the formula I

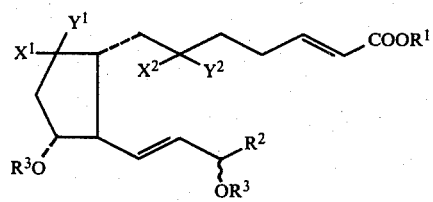

which are structurally related to the natural prostaglandins and in which $X^1$ and $Y^1$ as well as $X^2$ and $Y^2$, which may be identical or different, together denote oxygen or individually are hydrogen or hydroxyl;

$R^1$ denotes
(a) hydrogen or a linear or branched, saturated or unsaturated, aliphatic or cycloaliphatic hydrocarbon radical having up to 10 carbon atoms; or
(b) a physiologically acceptable metal ion or $NH_4^\pm$ ion, or an ammonium ion derived from a primary, secondary or tertiary amine;

$R^2$ denotes a linear or branched alkyl radical having from 1 to 7 carbon atoms in which a non-terminal $CH_2$ group can be replaced by oxygen, or which can be substituted with
(a) halogen or an α- or β-thienyl or furyl radical which in turn can be substituted 1 to 3 times in the nucleus by halogen, trifluoromethyl, and/or alkyl or alkoxy each having from 1 to 6 carbon atoms, or
(b) with an α- or β-thienyloxy or a cycloalkoxy radical having from 3 to 7 carbon atoms, which radicals may be substituted 1 to 3 times in the nucleus with halogen, trifluoromethyl and/or alkyl or alkoxy each having from 1 to 6 carbon atoms, or cycloalkyl having from 3 to 7 carbon atoms, $R^3$ denotes hydrogen or an easily detachable protective group, for example a tetrahydropyran-2-yl or tetrahydrofuran-2-yl group, optionally substituted by at least one alkyl group, or a 1-ethoxyethyl group.

Especially preferred substituents $R^1$ are hydrogen, methyl, ethyl, n-butyl, n-pentyl, n-hexyl, n-heptyl, 2-propyl, 2-butyl, 2-pentyl, 3-hexyl, 2-methylpropyl, 2-methylbutyl, 4,4-dimethylpentyl, 5,5-dimethylhexyl, cyclopentyl, cyclohexyl, cycloheptyl.

$R^2$ is particularly a linear or branched alkyl radical which is substituted as indicated above or in which a non-terminal $CH_2$-group is replaced by oxygen.

Especially preferred substituents $R^2$ are 1,1-dimethyl-2-butoxy-ethyl, 1,1-dimethyl-2-ethoxy-ethyl, 1,1-dimethyl-2-methoxy-ethyl, 1,1-dimethyl-cyclohexyloxymethyl, 1-fluorpentyl, 1-chlorpentyl, 5-fluorpentyl, 5-chlorpentyl, 3-thienyl-2-ethyl, 2-thienyl-2-ethyl, 3-(2-chlor-thienyl)-2-ethyl, 2-(5-chlor-thienyl)-2-ethyl, phenoxymethyl, 3-chlor-phenoxymethyl, 2-thienyloxymethyl, 3-(2-chlorthienyl)-oxymethyl, 2-(5-chlorthienyl)-oxymethyl, 3-furyl-2-ethyl, 2-furyl-2-ethyl.

The present invention also provides a process for the manufacture of compounds of formula I, which comprises (a) reacting a lactol of the formula II

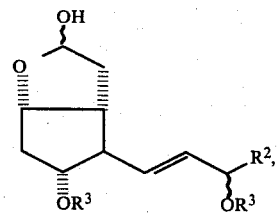

in which $R^2$ is as defined under formula I and $R^3$ denotes an easily detachable protective group, with a Grignard reagent of the formula III

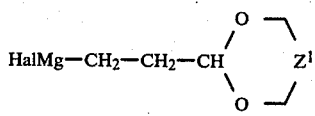

in which $Z^1$ denotes a $-CH_2$ group, a $-C(CH_3)_2$ group or a single bond and Hal stands for chlorine, bromine or iodine, to give an alcohol of the formula IV

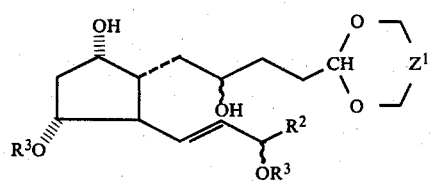

in which $R^2$, $R^3$ and $Z^1$ are as defined under formula II and $Z^1$ is as defined under formula III;

(b₁) detaching the protective groups from the alcohol of formula IV by acid hydrolysis, whereupon an aldehyde of the formula V is obtained

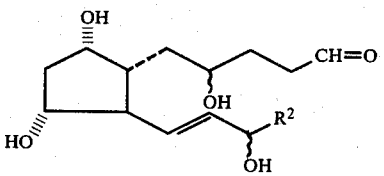

in which $R^2$ is as defined under formula I, ($c_1$) reacting the aldehyde of the formula V obtained with an ylide of the formula VI

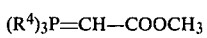    VI in which the radicals $R^4$ are identical or different and denote linear $C_1$-$C_4$alkyl or phenyl to give a compound of the formula VII

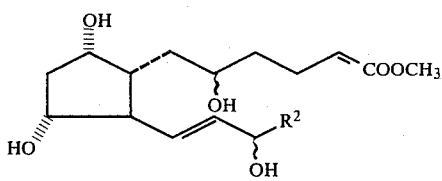    VII in which $R^2$ is as defined under formula I;

($d_1$) converting the alcohol of the formula IV by oxidation into a compound of the formula VIII

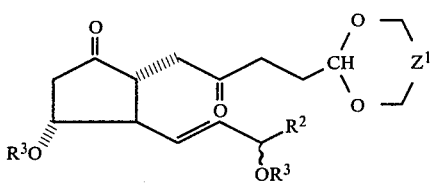    VIII in which $R^2$ and $R^3$ are as defined under formula I and $Z^1$ is as defined under formula III, ($e_1$) detaching the protective groups from the ketone of formula III by acid hydrolysis, whereupon an aldehyde of the formula IX is obtained

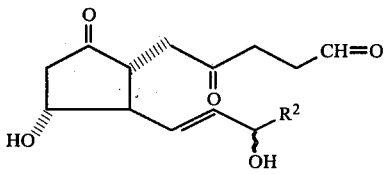    IX wherein $R^2$ is as defined under formula I, ($f_1$) reacting the aldehyde of the formula IX with the ylide of the formula VI

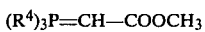    VI in which the radicals $R^4$, which are identical or different, denote linear $C_1$-$C_4$ alkyl or phenyl to give a compound of the formula X

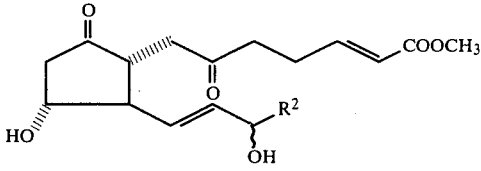    X in which $R^2$ is as defined under formula I, or ($a_2$) reacting a lactol of the formula II

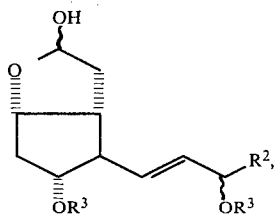    II in which $R^2$ and $R^3$ are as defined under formula I, with a Grignard compound of the formula XI

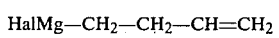    XI in which Hal denotes chlorine, bromine or iodine to give an alcohol of the formula XII

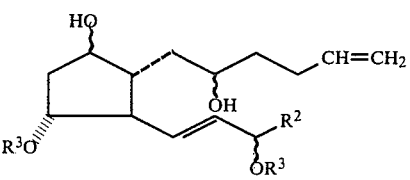    XII in which $R^2$ and $R^3$ are as defined under formula I, ($b_2$) oxidizing the alcohol of the formula XII to give a ketone of the formula XIII

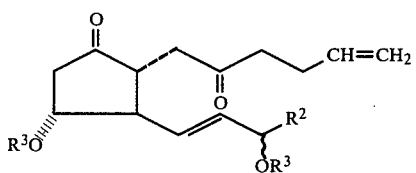    XIII in which $R^2$ and $R^3$ are as defined in formula I, ($c_2$) selectively oxidizing the terminal double bond in the diketone of formula XIII, whereupon a diol of the formula XIV

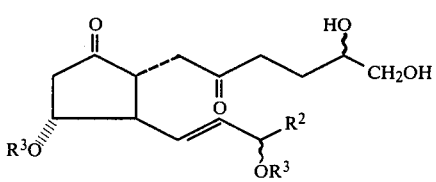    XIV in which $R^2$ and $R^3$ are as defined under formula I is obtained, ($d_2$) oxidizing the diol of the formula XIV to give a diketoaldehyde of the formula XV

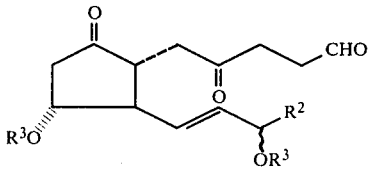    XV in which $R^2$ and $R^3$ are as defined under formula I, ($e_2$) reacting the diketoaldehyde of the formula XV

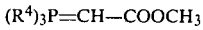    VI in which the radicals $R^4$, which are identical or different denote linear $C_1$-$C_4$alkyl or phenyl to give a compound of the formula XVI

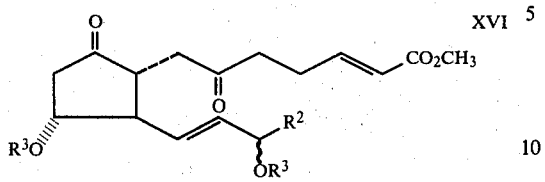

XVI in which $R^2$ and $R^3$ are as defined under formula I, or
(f$_2$) detaching the protective groups from the compound of formula XV by acid hydrolysis, whereupon an aldehyde of the formula IX is obtained.

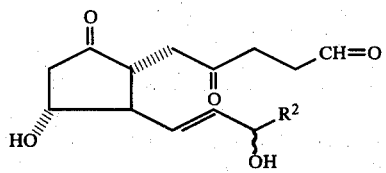

IX in which $R^2$ is as defined under formula I, and converting the compound obtained by process step (f$_1$) into a compound of the formula X, or
(g$_2$) in a compound of the formula XVI

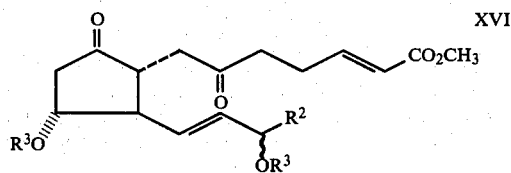

XVI in which $R^2$ and $R^3$ are as defined under formula I, optionally detaching the protective groups $R^3$ by acid hydrolysis, whereupon a compound of the formula X is obtained,
(h) optionally reducing a compound of the formula X with a complex metal hydride to give a compound of the formula VII,
(i) optionally converting a compound of the formula VII, X or XVI by hydrolysis into a compound of the formula I in which $R^1$ denotes hydrogen and $X^1$, $Y^1$, $X^2$, $Y^2$, $R^2$ and $R^3$ are as defined under formula I,
(k) optionally reducing a compound of the formula I, in which $R^1$ and $R^3$ denote hydrogen, $R^2$ is as defined under formula I and $X^1$ and $Y^1$ as well as $X^2$ and $Y^2$ together denote oxygen with a complex metal hydride to give a compound of the formula I in which $X^1$ and $Y^1$ as well as $X^2$ and $Y^2$ are different from each other and denote hydrogen or hydroxy
(l) optionally esterifying a compound of the formula I in which $X^1$, $X^2$, $Y^1$, $Y^2$ and $R^2$ are as defined under formula I and $R^1$ denotes hydrogen to give a compound of the formula I in which $X^1$, $X^2$, $Y^1$, $Y^2$ and $R^2$ are as defined under formula I and $R^1$ is not hydrogen,
(m) optionally converting a compound of the formula I in which $X^1$, $X^2$, $Y^1$, $Y^2$ and $R^2$ are as defined under formula I and $R^1$ denotes hydrogen into a physiologically acceptable metal or amine salt.

The aldehyde of the formula IX or XV is in an equilibrium with its inner semiacetal of the formula IX a

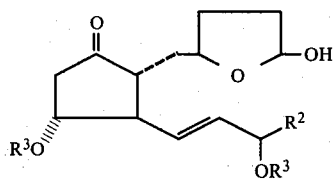

IX a

The compounds of the formula I in which $R^1$ denotes hydrogen according to process steps (a$_1$) to (f$_1$) and (i) can be prepared as described in detail in DE-OS 2,546,313. The compounds of the formula I in which $R^1$ is hydrogen are esterified by methods as disclosed in DE-OS 2,628,564.

The Grignard reagent of formula III can be prepared as described by S. Büchi, H. Wüst, J. Org. Chem. 34, 1121 (1969).

In general the compounds of formula I according to the invention are obtained in the form of their racemates, which can be separated into their optically active antipodes by the usual methods of racemate separation.

The starting compounds of the formula II can be prepared by the process described in DE-OS 2,416,193.

The process according to steps (a$_2$) to (e$_2$) likewise uses as a starting compound the lactol of the formula II

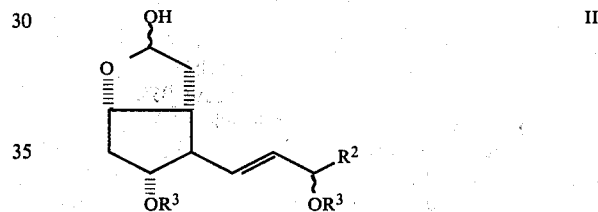

II which is reacted with a Grignard compound of the formula XI in an aprotic solvent at a temperature of from $-20°$ to $+60°$ C. to give a diol of the formula XII. According to a preferred embodiment of the reaction, a Grignard compound of the formula XI is prepared by allowing magnesium to act on a 4-halogenobutene-1,2 in tetrahydrofurane (THF) and then reacting the Grignard compound obtained at room temperature and for 24 hours with the lactol of the formula II.

The diketone of the formula XIII is obtained from the diol of the formula XII by oxidation with an oxidant, such as chromic acid, chromic acid-pyridine complex compounds, Jones reagent, pyridinium chlorochromate, pyridinium dichromate, and other oxidants requiring dimethyl sulfoxide or dimethyl sulfide as a reagent. The oxidation is preferably carried out in an aprotic solvent at a temperature in the range from $-60°$ C. to room temperature, more preferably $-60°$ to $-5°$ C., in an inert atmosphere. Suitable solvents are, for example, aromatic hydrocarbons such as benzene or toluene, or chlorinated aliphatic hydrocarbons such as carbon tetrachloride or methylene chloride.

In the compound of the formula XIII, the terminal double bond is selectively oxidized with an oxidant, for example osmium tetroxide, potassium permanganate, peracids, in a suitable solvent that cannot be oxidized itself, such as water and dioxane, at a temperature from $-20°$ C. to $+50°$ C., whereupon a diol of the formula XIV is obtained which, if desired, is isolated or further oxidized, optionally with the addition of periodic acid or the alkali metal salts thereof, to give an aldehyde of the formula XV. More particularly, the oxidation processes are carried out as described in "Advanced Organic Chemistry" (edition 1976), especially chapter B, pages 748 to 752 and 1087 to 1089.

The aldehyde of the formula XV obtained can be reacted according to Wittig without further purification to give a carboxylic acid ester of the formula XVI. According to a preferred embodiment this reaction is carried out as described in Fasciculus Helv.chim. acta XL, 1247 (1957).

The protective ether groups in a compound of the formula XV and XVI are detached by acid hydrolysis with aqueous organic acids under mild conditions, preferably in a 2% aqueous-alcoholic oxalic acid solution at 20° C. to 50° C. or by heating for 1 to 2 hours to 40° C. in 60 to 70% acetic acid, whereby an aldehyde of the formula IX or an ester of the formula X is obtained.

After filtration over a silica gel column, the aldehyde of the formula IX obtained can be reacted according to Wittig with an ylide of the formula VI to give a carboxylic acid ester of the formula X, preferably by the method indicated above.

The 15-S epimer is preferably separated from the 15-R epimer while in the form of an ester of the formula X, advantageously on silica gel (Merck$^{(R)}$, 70-230 mesh), in most cases the 15-S epimer being eluted after the 15-R epimer.

The ester of the formula X can be converted with a complex metal hydride such as lithium-aluminum hydride or sodium borohydride or with another suitable reducing agent into a compound of the formula I in which $X^1$, $Y^1$, and $X^2$, $Y^2$ each denote hydrogen or hydroxy and $X^1$ and $Y^1$ as well as $X^2$ and $Y^2$ are different from one another. The compound X is preferably reduced in an aprotic solvent at $-20°$ C. to room temperature using sodium borohydride. The isomers obtained in the reduction can be separated from each other over a silica gel column, preferably a ready-to-use column of Messrs.Merck.

Besides the compounds indicated in the examples, the following compounds can be produced, for example, by the process of the invention:

6,9,11,15-tetrahydroxy-16,16-dimethyl-18-oxa-(E)-2, (E)-13-prostadienoic acid;
11,15-dihydroxy-6,9-dioxo-16,16-dimethyl-18-oxa-(E)-2, (E)-13-prostadienoic acid;
11,15-dihydroxy-6,9-dioxo-16,16-dimethyl-18-oxa-(E)-2, (E)-13-prostadienoic acid ethyl ester,
6,9,11,15-tetrahydroxy-20-homo-(E)-2, (E)-13-prostadienoic acid;
11,15-dihydroxy-6,9-dioxo-20-homo-(E)-2, (E)-13-prostadienoic acid;
6,9,11,15-tetrahydroxy-20-nor-(E)-2, (E)-13-prostadienoic acid,
11,15-dihydroxy-6,9-dioxo-20-nor-(E)-2, (E)-13-prostadienoic acid,
6,9,11,15-tetrahydroxy-20-homo-(E)-2, (E)-13-prostadienoic acid propyl ester,
15-cyclohexyl-6,9,11,15-tetrahydroxy-16,17,18,19,20-pentanor-(E)-2, (E)-13-prostadienoic acid,
15-cyclohexyl-6,9-dioxo-11,15-hydroxy-16,17,18,19,20-pentanor-(E)-2, (E)-13-prostadienoic acid and the corresponding methyl ester,
16-chloro-6-keto-PGE$_1$ methyl ester,
16-fluor-6-keto-PGE$_1$,
16-chloro-6-keto-PGE$_1$ ethyl ester,
17-(2-thienyl)-18,19,20-trinor-6-keto-PGE$_1$,
17-[3-(chlorthienyl)]-18,19,20-trinor-6-keto-PGE$_1$ methyl ester,
16-phenoxy-17,18,19,20-tetranor-6-keto-PGE$_1$ ethyl ester,
16-(3-trifluormethyl-phenoxy)-17,18,19,20-tetranor-6-keto-PGE$_1$ n-butyl ester,
16-[3-(2-chlor)thienyloxy]-17,18,19,20-tetranor-6-keto-PGE$_1$ methyl ester,
16-(2-thienyloxy)-17,18,19,20-tetranor-6-keto-PGE$_1$ methyl ester,
17-(3-furyl)-18,19,20-trinor-6-keto-PGE$_1$,
15-cyclopentyl-16,17,18,19,20-pentanor-6-keto-PGE$_1$ propyl ester,
15-cyclopentyl-16,17,18,19,20-pentanor-6-keto-PGE$_1$,
17-oxa-6-keto-PGE$_1$ methyl ester,
16,16-dimethyl-17-oxa-21-homo-6-keto-PGE$_1$,
17-oxa-16,16,19-trimethyl-6-keto-PGE$_1$ n-butyl ester,
16,16-dimethyl-18-oxa-21-homo-6-keto-PGE$_1$,
19-oxa-6-keto-PGE$_1$ ethyl ester.

The compounds according to the invention are distinguished, on the one hand, by a spasmogenic action and, on the other, by an inhibiting action on the aggregation of thrombocytes, by hypotensive properties, by a dilating action on the coronary vessels and by an inhibition of the secretion of gastric juice. In comparison with the natural prostaglandins the compounds of the invention have a stronger and longer lasting effect. They can, therefore, be used as medicaments.

The compounds, according to the invention, of the formula I can be used in the form of the free acids, in the form of their physiologically acceptable inorganic or organic salts or in the form of esters.

The acid and salts or esters can be used in the form of their aqueous solutions or suspensions or as a solution or suspension in pharmacologically acceptable organic solvents, such as monohydric or polyhydric alcohols, such as, for example, ethanol, ethylene glycol or glycerol, oils, such as, for example, sunflower oil or cod-liver oil, ethers, such as, for example, diethylene glycol dimethyl ether, or polyethers, such as, for example, polyethylene glycols or in the presence of other pharmacologically acceptable polymer carriers, such as, for example, polyvinylpyrrolidone.

Formulations which can be used are the conventional galenic infusion or injection solutions and also tablets and preparations for local application such as ointments, emulsions, suppositories and especially aerosols.

A further use of the novel compounds is in combination with other active compounds. In addition to other suitable substances, these include, above all: secretolytics, for example bisolvon, β-sympathomimetics such as salbutamol and aludrin, antitussive agents such as codeine, fertility regulating hormones or releasing hormones such as LH-FSH, oestradiol, LH-RH, diuretics such as furosemide, antidiabetics such as glycodiazine, tolbutamide, glibenclamide, phenformin, buformin, metformin substances acting on the circulation in the broadest sense, for example coronary dilators such as chromonar or prenyl amine, hypotensive substances such as reserpine, α-methyl-dopa, or clonidine, antiarrhythmic agents, agents which lower the lipid level, geriatric preparations and other preparations which act on the metabolism, psychopharmacological agents, for example chlordiazepoxide, diazepam or meprobamate, vitamins, prostaglandins, prostaglandin analogs as well as prostaglandin antagonists and substances which inhibit prostaglandin biosynthesis, for example nonsteroid antiphlogistic agents.

The compounds of formula I according to the invention inhibit the aggregation of thrombocytes and have a hypotensive effect as ascertained, for example, by means of the aggregation of thrombocytes induced in vitro with arachidonic acid or by intravenous administration to non sleeping dogs in a dose of 0.01 to 1 mg/kg. The dosage unit for the treatment of human beings is, therefore, in the range of from 0.01 to 1 mg/kg, preferably 0.05 to 0.5 mg/kg, and the daily dose ranges from 0.03 to 3 mg/kg, preferably 0.15 to 1.5 mg/kg.

The compounds of formulae IV, V, VII, VIII, IX, X, XII, XIII, XIV, XV and XVI are novel and valuable intermediates for the manufacture of compounds of the formula I.

The following examples illustrate the invention.

EXAMPLE 1

1-Bromo-2(1,3-dioxo-2-cyclohexyl)-ethane 350 g of hydrogen bromide were introduced at $-5°$ C. into 851 g of 1,3-propanediol. Next, 165 g of 195 ml of acrolein were added dropwise while cooling to a temperature not exceeding 10° C. Stirring was continued for 1 hour at room temperature, whereupon the mixture was extracted 4 times with n-hexane. The organic phase was separated and stirred for 2 hours with solid $NaHCO_3$. The mixture was filtered with suction and the solvent removed under reduced pressure. 408 g of crude product were obtained. It was fractionated in a 10 cm column. Yield: 313 g of colorless liquid having a boiling point of 89° to 91° C. under 15 mm of Hg.

| NMR: | $\delta 1,1-2,4$ (m,4) $-CH_2-$, $-CH_2-CH <$ ; |
|---|---|
| | $\delta 3,3-4,3$ (m,6) $-CH_2-Br$, $-CH_2-O-$ |
| | $\delta 4,6$ (t,1) $-O-CH-O-$ |

EXAMPLE 2a

2-Oxa-3-hydroxy-6(3-tetrahydropyranyloxy-1-octenyl)-7-tetrahydropyranyloxy-bicyclo[3,3,0]octane (II)

10.32 g (0.025 mol) of 2-oxa-3-oxy-6(3-tetrahydropyranyl-oxy-1-octenyl)-7-tetrahydropyranyloxy-bicyclo[3,3,0]octane, prepared as described in DE-OS 2,416,193, were taken up in 250 ml of absolute toluene and cooled to $-70°$ C. 29.25 ml of 20% diisobutylaluminum hydride solution in absolute toluene were then added dropwise within 1 hour. Stirring of the mixture was continued for 2 hours at $-70°$ C. Next, 2.5 ml of acetic acid in toluene were added dropwise, the mixture was allowed to warm up to 0° C. and 100 ml of saturated sodium chloride solution were added. The mixture was filtered over a clarifying layer and ether/$H_2O$ was added to the filtrate. The organic phase was separated, dried and concentrated under reduced pressure.

Yield: 9.4 g of colorless oil.

Thin layer chromatogram $R_f=0.06$ (benzene/ethyl acetate 4:1)

IR spectrum (NaCl plates): 3400 (OH band) 2930 no carbonyl band; 1450, 1200, 1122, 1035 and 980 $cm^{-1}$

EXAMPLES 2b TO 2h

The following compounds were prepared in the manner described in Example 2a by reduction with diisobutylaluminum hydride.

| EXAMPLE 2 | $R^2$ | $R_f$ values in ethyl acetate |
|---|---|---|
| b | 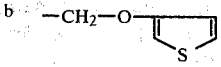 | 0.82 |
| c | 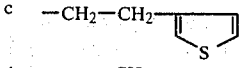 | 0.78 |
| d | 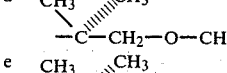 | 0.53 ethyl acetate 2 |
| e | 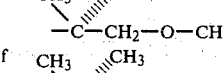 | 0.92 cyclohexane 1 |
| f | 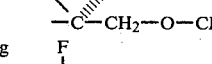 | 0.90 |
| g | 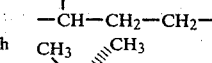 | 0.86 |
| h | 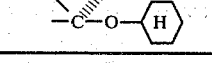 | 0.91 |

EXAMPLE 3

1[4(3-hydroxy-1(1,3-dioxa-2-cyclohexyl)-butyl]-2-(3-tetrahydropyranyloxy-1-octenyl)-3-(tetrahydropyranyloxy)-5-hydroxy-cyclopentane (IV)

170 g of magnesium were etched with iodine crystals, 5 ml of absolute THF were added and 1 g of 1-bromo-2(1,3-dioxo-2-cyclohexyl)-ethane (Example 1) in 5 ml of absolute THF was dropped in over a period of 20 minutes. The reaction started on slight heating. Stirring was continued for 2 hours at 50° C., whereupon 440 mg of 2-oxa-3-hydroxy-6(3-tetrahydropyranyloxy-1-octenyl)-7-tetrahydropyranyloxy-bicyclo[3,3,0]-octane (Example 2) in 10 ml of absolute diethyl ether were added dropwise. The mixture was then stirred for another 3 hours at room temperature. Next, ice and dilute hydrochloric acid were added, the mixture was saturated with NaCl and extracted with ether. The organic phase was washed twice with NaCl/bicarbonate solution, dried with $MgSO_4$ and concentrated under reduced pressure.

Yield: 610 mg of crude product. The impurities were separated over a silica gel column using ether as an eluant.

Yield: 400 mg of slightly yellow oil $R_f=0.06$ (cyclohexane 50/ethyl acetate 50/glacial acetic acid 2)

| NMR:$\delta$ | 0.7–2.5 (m,35) $-CH_2-$, $-CH-$; |
|---|---|
| | 3.1–4.3 (m,14) $-CH_2-O-$, $-CH-O-$, OH; |
| | 4.35–4.8 (m,3) $-O-CH-O$, |
| | 5.2–5.6 (m,2) olefinic protons |

EXAMPLE 4

1[4(1-Formyl-3-hydroxy)-butyl]-2(3-hydroxy-1-octenyl)-3,5-dihydroxy-cyclopentane (V)

390 mg of 1[4(3-hydroxy-1(1,3-dioxa-2-cyclohexyl)-butyl]-2-(3-tetrahydropyranyl-oxy-1-octenyl)-3(tetrahydropyranyl-oxy)-5-hydroxy-cyclopentane (Example 3), 5 ml of dimethyl glycol, 5 ml of water and 1 ml of saturated oxalic acid solution were stirred for 13 hours at 50° C. The mixture was cooled, 10 ml of saturated sodium chloride solution were added, and the whole was saturated with NaCl and extracted with ethyl acetate. The organic phase was washed once with saturated NaCl/bicarbonate solution, dried over MgSO₄ and concentrated under reduced pressure.

The impurities were separated in a silica gel column using as an eluant first ether/ethyl acetate 1:1 and then ethyl acetate/glacial acetic acid 99:1.

Yield 200 mg of a slightly yellow oil; 2 isomers R$_f$=0.19 and 0.13 (ethyl acetate/glacial acetic acid 9:1).

| NMR:δ | 0.8–2.7 (m,21) —CH₂—, —CH—; |
| --- | --- |
| | 3.5–4.6 (m,7) —CH—O—, OH; |
| | 5.4–5.7 (m,2) olefinic protons |

EXAMPLE 5

6,9,11,15-tetrahydroxy-(E)-2, (E)-13-prostadienic acid methyl ester (VII)

190 mg of 1[4(1-formyl-3-hydroxy)-butyl]-2(3-hydroxy-1-octenyl)-3,5-dihydroxy-cyclopentane (V) (Example 4) and 290 mg of carbomethoxymethylene-triphenylphosphorane (VI) (cf. v. Fasciculus Helv. Chim. acta XL, page 1247 (1957)) in 10 ml of absolute benzene were stirred for 16 hours at room temperature and under N₂. The mixture was then concentrated and the residue was purified in a column of silica gel using as an eluant first ether, then ether/ethyl acetate and finally ethyl acetate/methyl acetate.

Yield 43 mg of light yellow oil, 2 isomers R$_f$0.26 and 0.22 (ethyl acetate/glacial acetic acid 9:1).

| NMR:δ | 0.8–2.5 | (m,21) —CH₂—, —CH—, |
| --- | --- | --- |
| | 2.6–3.2 | (m,4) OH |
| | 3.5–4.4 | (m,4) —CH—OH, |
| | 3.7 | (s,3) OCH₃, |
| | 5.4–6.1 | (m,2) olefinic protons |

EXAMPLE 6a 6,9,11,15-tetrahydroxy-(E)-2, (E)-13-prostadienic acid (I)

300 mg of 6,9,11,15-tetrahydroxy-(E)-2, (E)-13-prostadienic acid methyl ester (VII) (Example 5) were dissolved in 10 ml of methanol and 3 equivalents of 0.5 N sodium hydroxide solution were added. The mixture was stirred for 8 hours at room temperature and the course of reaction was followed by thin layer chromatogram. When the saponification was complete, the solvent was cautiously removed under reduced pressure, ethyl acetate/water were added to the residue and the mixture was acidified to pH 4 to 5 with 1 N citric acid. The organic phase was then separated, dried over MgSO₄ and concentrated under reduced pressure.

Yield: 270 mg of yellow brown oil which was purified by chromatography on a silica gel column using ethyl acetate/glacial acetic acid 95:5.

Yield of pure product: 160 mg of light yellow oil

| NMR:δ | 0.8–2.5 (m,21) —CH₂—, —CH—, |
| --- | --- |
| | 3.5–4.3 (m,4) —CH—OH, |
| | 4.5–5.3 (broad signal, 5) OH, COOH |
| | 5.4–6.1 (m,2) olefinic protons |

| | 6.6–7.1 (m,2) olefinic protons |
| --- | --- |

EXAMPLES 6b TO 6h

In the manner described in Example 6a the following compounds of formula I with X¹, Y¹, X², Y² being hydrogen or hydroxy and R¹=hydrogen were prepared by ester saponification using as starting compounds the compounds of

EXAMPLES 21b TO 21h.

| EXAMPLE 6 | R² |
| --- | --- |
| b |  |
| c |  |
| d | CH₃ CH₃<br>\\ //<br>—C—CH₂—O—CH₂—CH₃ |
| e | CH₃ CH₃<br>\\ //<br>—C—CH₂—O—CH₃ |
| f | CH₃ CH₃<br>\\ //<br>—C—CH₂—O—CH₂—CH₂—CH₃ |
| g | F<br>\|<br>—CH—CH₂—CH₂—CH₂—CH₃ |
| h | CH₃ CH₃<br>\\ //<br>—C—O— |

EXAMPLE 7

1[4(3-oxo-1(1,3-dioxa-2-cyclohexyl)-butyl]-2(3-tetrahydropyranyloxy-1-octenyl)-3(tetrahydropyranyloxy)-5-oxo-cyclopentane (VIII)

0.45 g of 1[4(3-hydroxy-1(1,3-dioxa-2-cyclohexyl)-butyl]-2(3-tetrahydropyranyloxy-1-octenyl)-3(tetrahydropyranyloxy)-5-hydroxy-cyclopentane (IV) (Example 3) were dissolved in 30 ml of acetone. At −20° to −25° C., 2 ml of Jones reagent (2.1 g of chromic acid, 6 ml of water, 1.7 ml of concentrated sulfuric acid) were added under argon. The mixture was stirred for 30 minutes, 3 ml of isopropanol were added and stirring was continued for a further 10 minutes to destroy the oxidation reagent in excess. Next, 100 ml of methylene chloride and 100 ml of water were added, the mixture was shaken and the phases were separated. The organic phase was dried with MgSO₄ and the solvent was removed under reduced pressure at a temperature of at most +5° C. 0.32 g of compound VIII in the form of an almost colorless clear oil was obtained.

Thin layer chromatogram (ethyl acetate/acetic acid 97.5:2.5) on silica gel plates of Messrs. Merck. R$_f$=0.75

EXAMPLE 8

1[4(1-Formyl-3-oxo)-butyl]-2(3-hydroxy-1-octenyl)-3-hydroxy-cyclopentane-5-one (IX)

280 mg of 1[4(1-formyl-3-hydroxy)-butyl]-2(3-hydroxy-1-octenyl)-3,5-dihydroxy-cyclopentane (V) (Example 4), 5 ml of dimethyl glycol, 5 ml of water and 1 ml of saturated oxalic acid solution were stirred for 13 hours at 50° C. The mixture was cooled, 10 ml of saturated sodium chloride solution were added, the whole was saturated with NaCl and extracted with ethyl acetate. The organic phase was washed once with saturated NaCl/bicarbonate solution, dried over MgSO$_4$ and concentrated under reduced pressure. The impurities were separated over a silica gel column using as eluent first ethyl ether/ethyl acetate 1:1 and then ethyl acetate/glacial acetic acid 99:1.

Yield: 170 mg of colorless oil.

Thin layer chromatogram (ethyl acetate/glacial acetic acid 97.5:2.5) on silica gel plates of Messrs. Merck; R$_f$=0.55

EXAMPLE 9a 6,9-Dioxo-11,15-dihydroxy-(E)-2, (E)-13-prostadienoic acid methyl ester (X)

170 mg of 1[4(1-formyl-3-oxo)-butyl]-2(3-hydroxy-1-octenyl)-3-hydroxy-cyclopentan-5-one (IX) (Example 8) and 240 mg of carbomethoxymethylene-triphenylphosphorane (VI) (cf. v. Fasciculus Helv. chim. acta XL, page 1247 (1957)) in 15 ml of absolute benzene were stirred for 16 hours at room temperature and under N$_2$. The mixture was concentrated and the residue purified in a silica gel column using as an eluant first ethyl ether, then ethyl ether/ethyl acetate and finally ethyl acetate/methyl acetate.

Yield, 123 mg of light yellow oil, 2 isomers

Thin layer chromatogram: silica gel plates of Messrs. Merck. R$_f$ values 0.5 and 0.45 (ethyl acetate/glacial acetic acid 97.5:2.5)

| NMR:δ | 0.8–2.5 | (m,21) | —CH$_2$—, —CH—, |
|---|---|---|---|
| | 3.0–3.5 | (m,2) | OH |
| | 3.5–4.4 | (m,2) | —CH—OH, |
| | 3.8 | (s,3) | OCH$_3$, |
| | 5.5–6.2 | (m,2) | olefinic protons |
| | 6.6–7.2 | (m,2) | olefinic protons |

EXAMPLES 9b TO 9h

In the manner described in Example 9a the following compounds were prepared by a Wittig reaction from the compounds of Examples 19b to 19h (formula X)

| EXAMPLE 9 | R$^2$ | δ-values NMR (CDCl$_3$) |
|---|---|---|
| b | —CH$_2$—O—[thiophene] | 0.95–3.0 (m, 12H) —CH$_2$—, —CH—, OH; 3.6 (s, H) —OCH$_3$; 3.9 (d, 2H) —CH$_2$—O thiophen; 4.1–4.6 (m, 2H) —CH—OH; 5.4–5.8 (m, 2H) olefinic protons; 6.0–7.3 (m, 5H) thiophene and olefinic protons |
| c | —CH$_2$—CH$_2$—[thiophene] | 0.95–3.0 (m, 16H) —CH$_2$—, —CH—, OH; 3.6 (s, 3H) —OCH$_3$; 3.7–4.5 (m, 2H) —CH—OH; 5.3–5.9 (m, 2H) olefinic protons; 6.0–7.3 (m, 5H) olefinic protons and thiophene |
| d | CH$_3$ \ C—CH$_2$—OCH$_2$—CH$_3$ / CH$_3$ | 0.9 (s, 6H) C(CH$_3$)$_2$; 1.15 (t, 3H) —CH$_2$—CH$_3$; 1.4–2.95 (m, 16H) —CH$_2$—; —CH—, OH; 3.3 (s, 2H) —OCH$_2$—; 3.5 (q, 2H) —OCH$_2$CH$_3$; 3.6 (s, 3H) —OCH$_3$; 3.8–4.5 (m, 2H) —CH—OH; 5.5–7.1 (m, 4H) olefinic protons |
| e | CH$_3$ \ C—CH$_2$—OCH$_3$ / CH$_3$ | 0.9 (s, 6H) C(CH$_3$)$_2$; 1.1–2.9 (m, 12H) —CH$_2$—; —CH—, OH; 3.2 (s, 2H) —CH$_2$OCH$_3$; 3.3 (s, 3H) —CH$_2$—OCH$_3$; 3.6 (s, 3H) —CO$_2$CH$_3$; 3.7–4.5 (m, 2H) —CH—OH; 5.5–7.1 (m, 4H) olefinic protons |
| f | CH$_3$ \ C—CH$_2$—O—CH$_2$—CH$_2$—CH$_3$ / CH$_3$ | 0.9 (s + t, 9H) —C(CH$_3$)$_2$, CH$_3$; 1.2–2.9 (m, 14H) —CH$_2$—, —CH—, OH; 3.25 (s, 2H) —CH$_2$—O—, 3.35 (t, 2H) —O—CH$_2$—CH$_2$—CH$_3$; 3.6 (s, 3H) —OCH$_3$; 3.7–4.4 (m, 2H) —CH—OH; 5.5–7.1 olefinic protons |
| g | F \|  —CH—CH$_2$—CH$_2$—CH$_2$—CH$_3$ | 0.9 (t, 3H) CH$_3$; 3.6 (s, 3H) CO$_2$CH$_3$; 5.4–7.1 (m, 4H) olefinic protons |

-continued

| EXAMPLE 9 | R² | δ-values NMR (CDCl₃) |
|---|---|---|
| h | CH₃ ⁄⁄⁄⁄CH₃ \C—O—⟨H⟩ | 1.05 (d, 6H) —C(CH₃)₂; 0.9–3.1 (m, 19H) —CH₂—, —CH—, OH; 3.6 (s, 3H) —CO₂CH₃; 3.4–4.3 (m, 3H) —CH—OH, —CH—O; 5.5–7.1 (m, 4H) olefinic protons |

EXAMPLE 10a 6,9-dioxo-11,15-dihydroxy-(E)-2, (E)-13-prostadienoic acid (I)

123 mg of 6,9-dioxo-11,15-dihydroxy-(E)-2, (E)-13-prostadienoic acid methyl ester (Example 9) were dissolved in 15 ml of methanol and 4 equivalents of 0.5 N sodium hydroxide solution were added. The mixture was stirred for 8 hours at room temperature and the course of the reaction was followed by thin layer chromatogram. When the saponification was complete, the solvent was cautiously removed under reduced pressure, ethyl acetate/water was added to the residue and the whole was acidified to pH 4 to 5 with 1 N citric acid. The organic phase was separated, dried over MgSO₄ and concentrated under reduced pressure.

Yield: 130 mg of yellow brown oil which was purified by chromatography on a silica gel column using ethyl acetate/glacial acetic acid 95:5.

Yield: of pure product 86.0 mg of light oil

| NMR:δ | 0.8–2.5 | (m, 21) | —CH—, —CH—, |
|---|---|---|---|
| | 3.5–4.3 | (m, 2) | —CH—OH, |
| | 4.8–5.4 | (broad signal) | OH, COOH |
| | 5.4–6.2 | (m, 2) | olefinic protons |
| | 6.5–7.1 | (m, 2) | olefinic protons |

EXAMPLES 10b TO 10h

In the manner described in Example 10a the following compounds of formula I with X¹=Y¹=X²=Y² being oxygen were prepared by ester saponification from the compounds of examples 9b to 9h.

| EXAMPLE 10 | R² |
|---|---|
| b | —CH₂—O—⟨S⟩ |
| c | —CH₂—CH₂—⟨S⟩ |
| d | CH₃ ⁄⁄⁄⁄CH₃ \C—CH₂—O—CH₂—CH₃ |
| e | CH₃ ⁄⁄⁄⁄CH₃ \C—CH₂—O—CH₃ |
| f | CH₃ ⁄⁄⁄⁄CH₃ \C—CH₂—O—CH₂—CH₂—CH₃ |
| g | F \| —CH—CH₂—CH₂—CH₂—CH₃ |
| h | CH₃ ⁄⁄⁄⁄CH₃ \C—O—⟨H⟩ |

EXAMPLE 11a 6,9,11,15-Tetrahydroxy-(E)-2, (E)-13-prostadienoic acid ethyl ester (I)

While cooling with ice, 5 ml of a 1 molar diazoethane solution in ether were added to a solution of 80 mg of 6,9,11,15-tetrahydroxy-(E)-2, (E)-13-prostadienoic acid (I) (Example 6) in 6 ml of ether. Stirring of the mixture was continued for 30 minutes, whereupon the solvent was evaporated under reduced pressure together with the excess of diazoethane. The product obtained was chromatographically pure.

| NMR analogous to Example 6, | | | |
|---|---|---|---|
| Ester:δ | 1.25 | (t, 3) | —COOCH₂CH₃; |
| | 4.25 | (q, 2) | —COOCH₂CH₃ |

EXAMPLES 11b TO 11h

In the manner described in Example 11a the compounds according to Examples 6b to 6h could be converted into the corresponding ethyl esters.

EXAMPLE 12a 6,9-Dioxo-11,5-dihydroxy-(E)-2, (E)-13-prostadienoic acid ethyl ester (I)

While cooling with ice, 5 ml of a 1 molar diazoethane solution in ether were added to a solution of 50 mg of 6,9-dioxo-11,15-dihydroxy-(E)-2, (E)-13-prostadienoic acid (Example 10) in 10 ml of ether. Stirring of the mixture was continued for 30 minutes, whereupon the solvent was evaporated under reduced pressure together with the excess amount of diazoethane. The product obtained was chromatographically pure.

| NMR analogous to Example 10 | | | |
|---|---|---|---|
| ester:δ | 1.24 | (t, 3) | —COOCH₂CH₃, |
| | 4.25 | (q, 2) | —COOCH₂CH₃ |

EXAMPLES 12b TO 12h

In the manner described in Example 12a the compounds of the Examples 10b to 10h could be converted into the corresponding ethyl esters.

EXAMPLE 13a 6,9,11,15-Tetrahydroxy-(E)-2, (E)-13-prostadienoic acid thromethamine salt (I)

An ethanolic solution of 22.9 mg of thromethamine base was added to a solution of 70 mg of 6,9,11,15-tetrahydroxy-(E)-2, (E)-13-prostadienoic acid (Example 6) in 4 ml of ethanol and the solvent was evaporated, finally in a high vacuum.

Yield 92 mg of thromethamine salt (I) in the form of "oily" crystals.

EXAMPLES 13b TO 13h

In the manner described in Example 13a the compounds according to Examples 6b to 6h could be converted into the corresponding salts.

EXAMPLE 14a 6,9-Dioxo-11,15-dihydroxy-(E)-2, (E)-13-prostadienoic acid thromethamine salt (I)

An ethanolic solution of 14.9 mg of thromethamine base was added to a solution of 46 mg of 6,9-dioxo-11,15-dihydroxy-(E)-2, (E)-13-prostadienoic acid (Example 10) in 3 ml of ethanol, whereupon the solvent was evaporated, finally in a high vacuum.

Yield 59.5 mg of thromethamine salt (I)

EXAMPLES 14b TO 14h

In the manner described in Example 14a the compounds according to Examples 10b to 10h could be converted into the corresponding salts.

EXAMPLE 15a

1[6(5-Hydroxy)-hex-1-enyl]-2-(3-tetrahydropyranyloxy-1-octenyl)-3-(tetrahydropyranyloxy)-5-hydroxy-cyclopentane (XII)

250 mg of magnesium were etched with 0.2 ml of 1,2-bromoethane, 5 ml of absolute THF were added and 1.1 g of 4-bromobutene-1,2 in 5 ml of absolute THF were dropped in over a period of 20 minutes. The reaction started on slight heating. Stirring of the mixture was continued for 3 hours at room temperature, whereupon 0.88 g of 2-oxa-3-hydroxy-(3-tetrahydropyranyloxy-1-octenyl)-7-tetrahydropyranyloxy-bicyclo[3,3,0]-octane (Example 2) in 10 ml of absolute diethyl ether were added dropwise. Stirring of the mixture was then continued for 24 hours at room temperature. Next, ice and dilute hydrochloric acid were added, the whole was saturated with NaCl and extracted with ether. The organic phase was washed twice with NaCl-/bicarbonate solution, dried with $MgSO_4$ and concentrated under reduced pressure.

Yield of crude product 1.0 g. The crude product was used for the following step without purification $R_f$ 0.13 benzene/ethyl acetate 1:1

| NMR:δ | 5.2–5.8 (m, 2H) | olefinic protons |
| --- | --- | --- |
| | 5.2–4.5 (3m, 5H) | olefinic protons $-CH\begin{matrix}O\\ \\O\end{matrix}$ |
| | 4.5–3.0 (m, 8H) | OH; $-CH-O$ |
| | 2.7–0.8 (m, 33) | $-CH_2-$; $-CH-$ |

EXAMPLES 15b TO 15h

In the manner described in Example 15a the compounds according to Examples 2b to 2h could be converted into the following compounds by the Grignard reaction with a 4-halogeno-butene-1,2 (formula XII)

| EXAMPLE 15 | $R^2$ | δ-values NMR ($CDCl_3$) |
| --- | --- | --- |
| b | $-CH_2-O-\text{thiophen}$ | 3.9 (d, 2H) $-CH_2-O-$thiophen 4.1–4.6 (m, 2H); 4.6–5.2 (3m, 5H) olefinic protons; $-CH\begin{matrix}O-\\ \\O-\end{matrix}$ |
| c | $CH_2-CH_2-\text{thiophene}$ | 5.2–5.8 (m, 2H) olefinic protons, 6.1–7.3 (m, 3H) thiophene 4.6–5.2 (3m, 5H) olefinic protons, 5.4–5.8 (m, 2H) olefinic protons, 6.8–7.3 (m, 3H) thiophene |
| d | $-C(CH_3)(CH_3)-CH_2-O-CH_2-CH_3$ | 0.9 (s, 6H) $C(CH_3)_2$; 1.15 (t, 3H) $-CH_2-CH_3$ 4.6–5.2 (3m, 5H) and 5.4–5.8 (m, 2H) olefinic protons and $-CH\begin{matrix}O\\ \\O\end{matrix}$ |
| e | $-C(CH_3)(CH_3)-CH_2-O-CH_3$ | 0.9 (s, 6H) $-C-(CH_3)_2$; 3.2 (s, 2H) $-CH_2-OCH_3$; 3.3 (s, 3H) $-CH_2OCH_3$ 4.6–5.8 (4m, 7 () olefinic protons and $-CH\begin{matrix}O\\ \\O\end{matrix}$ |

-continued

| EXAMPLE 15 | R² | δ-values NMR (CDCl₃) |
|---|---|---|
| f | CH₃  CH₃<br>  \\ /<br>  —C—CH₂—O—CH₂—CH₂—CH₃ | 0.9 (s + t) —(CCH₃)₂; CH₃; 4.6–5.2 (3m, 5H); 5.4–5.8 (m, 2H) olefinic protons and —CH(O)(O) |
| g | F<br> \|<br>—CH—CH₂—CH₂—CH₂—CH₃ | 0.95 (t, 3H) CH₃; 4.6–5.2 (3m, 5H) 5.4–5.8 (m, 2H) olefinic protons and —CH(O)(O) |
| h | CH₃  CH₃<br>  \\ /<br>  —C—O—⟨H⟩ | 1.05 (d, 6H) —(CCH₃)₂; 4.5–5.2 (3m, 5H), 5.4–5.8 (m, 2H) olefinic protons and —CH(O)(O) |

EXAMPLE 16a

1[6-(5-oxo)-hex-1-enyl]-2[3-tetrahydropyranyloxy-1-octenyl]-3-(tetrahydropyranyloxy)-5-oxo-cyclopentane (XIII)

2.1 ml of DMSO were added dropwise at −60° C. to 20 ml of CH₂Cl₂ and then 2.8 ml of trifluoroacetic acid anhydride in 10 ml of CH₂Cl₂ were added at the same temperature. Stirring of the mixture was continued for 20 minutes, whereupon 1.0 g of 1[6(5-hydroxy)-hex-1-enyl]-2[3-tetrahydropyranyloxy-1-octenyl]-3-(tetrahydropyranyloxy)-5-hydroxy-cyclopentane (XII) in 10 ml of CH₂Cl₂ were added dropwise at −70° C. The mixture was stirred for a further 20 minutes, whereupon 10 ml of triethylamine were added. Stirring was continued for 30 minutes at −60° C., whereupon the temperature was slowly raised to room temperature. 30 ml of saturated sodium chloride solution were added and the mixture was extracted with ethyl acetate. The organic phase was washed once with saturated NaCl/bicarbonate solution, dried over MgSO₄ and concentrated under reduced pressure.

Impurities were removed in a silica gel column with cyclohexane/ethyl acetate 2:1 Yield: 855 mg of oil

| NMR: | 5.8–4.4 | (4m, 7H) |
|---|---|---|
| | 4.2–3.0 | (m, 7H) |
| | 3–2 | (m, 9H) |
| | 2–0.8 | (m and 1t, 22H) |

EXAMPLES 16b TO 16h

In the manner described in Example 16a the compounds according to Examples 15b to 15h could be converted by oxidation into the following compounds (formula XIII)

| EXAMPLE 16 | R² | Rf values in ethyl acetate |
|---|---|---|
| b | —CH₂—O—⟨S⟩ | 0.63 |
| c | —CH₂—CH₂—⟨S⟩ | 0.57 |
| d | CH₃  CH₃<br> \\ /<br>—C—CH₂—O—CH₂—CH₃ | 0.80 |
| e | CH₃  CH₃<br> \\ /<br>—C—CH₂—O—CH₃ | 0.68 |
| f | CH₃  CH₃<br> \\ /<br>—C—CH₂—O—CH₂—CH₂—CH₃ | 0.66 |
| g | F<br>\|<br>—CH—CH₂—CH₂—CH₂—CH₃ | 0.60 |
| h | CH₃  CH₃<br> \\ /<br>—C—O—⟨H⟩ | 0.070 |

EXAMPLE 17a

1[6(1,2-Dihydroxy-5-oxo)-hexyl]-2[3-tetrahydropyranyloxy-1-octenyl]-3-(tetrahydropyranyloxy)-5-oxocyclopentane (XIV)

78.5 mg of 1[6(5-oxo)-hex-1-enyl]-2[3-tetrahydropyranyloxy-1-octenyl]-3-(tetrahydropyranyloxy)-5-oxocyclopentane (XIII) were dissolved in 3 ml of absolute pyridine, 41 mg of osmium tetroxide were added at 0° C. and the mixture was stirred for 4 hours at 0° C. After said time, 90 mg of NaHSO₃ dissolved in 1 ml of water were added dropwise and the mixture was stirred for one hour at room temperature. Next, 10 ml of saturated NaCl solution were added, the mixture was extracted and the organic phase washed with saturated NaCl solution, dried over MgSO₄ and concentrated under reduced pressure. The crude product was washed three times with toluene.

The reaction product was freed from unreacted starting components over a silica gel column using first cyclohexane/ethyl acetate 1:1 and then ethyl acetate. From 41 mg of crude product, 32 mg of pure compound were obtained.

| NMR: | 5.5 | (m, 2H) |
|---|---|---|
| | 4.6 | (m, 2H) |
| | 4.4–3 | (m, 10H) |
| | 2.9–0.8 | (m and 1t, 34H) |

EXAMPLES 17b TO 17h

In the manner described in Example 17a the compounds according to Examples 16b to 16h could be converted by oxidation into the following diols (formula XIV)

| EXAMPLE 17 | $R^2$ | $R_f$ values in ethyl acetate |
|---|---|---|
| b | $-CH_2-O-\text{(thiophene)}$ | 0.15 |
| c | $-CH_2-CH_2-\text{(thiophene)}$ | 0.10 |
| d | $-C(CH_3)_2-CH_2-O-CH_2-CH_3$ | 0.3 |
| e | $-C-CH_2-O-CH_3$ | 0.27 |
| f | $-C(CH_3)_2-CH_2-O-CH_2-CH_2-CH_3$ | 0.24 |
| g | $-CHF-CH_2-CH_2-CH_2-CH_3$ | 0.18 |
| h | $-C(CH_3)_2-O-\text{(C}_6\text{H}_{11})$ | 0.31 |

EXAMPLE 18a

1[4(4-Formyl-3-oxo)-butyl]-2[3-tetrahydropyranyloxy-1-octenyl]-3-(tetrahydropyranyloxy)-5-oxo-cyclopentane (XV)

329 mg of 1[6(1,2-dihydroxy-5-oxo)-hexyl]-2[3-tetrahydropyranyloxy-1-octenyl]-3-(tetrahydropyranyloxy)-5-oxocyclopentane (XIV) were dissolved in 20 ml of dioxane and 65 ml of water, 775 mg of sodium periodate were added and the whole was stirred for 30 minutes at room temperature. For working up, 30 ml of saturated NaCl solution were added and the mixture was extracted 4 times with 50 ml each of ether, washed with saturated NaCl solution, dried over MgSO$_4$ and concentrated under reduced pressure.

Yield: 300 mg. The aldehyde obtained was used for the further steps without purification.

$R_f$ value 0.48 ethyl acetate

| NMR: | 9.75 | (s, 1H) —CHO |
|---|---|---|
| | 5.5 | (m, 2H) |
| | 4.6 | (m, 2H) |
| | 4.4–3 | (m, 8H) |
| | 2.9–2.1 | (m, 1OH) |
| | 2–0.8 | (m and 1t, 21H) |

EXAMPLES 18b TO 18h

In the manner described in Example 18a the compounds according to Examples 17b to 17h could be converted into the following compounds by selective splitting of the diols.

| EXAMPLE 18 | $R^2$ | $R_f$ values in ethyl acetate |
|---|---|---|
| b | $-CH_2-O-\text{(thiophene)}$ | 0.41 |
| c | $-CH_2-CH_2-\text{(thiophene)}$ | 0.37 |
| d | $-C(CH_3)_2-CH_2-O-CH_2-CH_3$ | 0.53 |
| e | $-C(CH_3)_2-CH_2-O-CH_3$ | 0.45 |
| f | $-C(CH_3)_2-CH_2-O-CH_2-CH_2-CH_3$ | 0.46 |
| g | $-CHF-CH_2-CH_2-CH_2-CH_3$ | 0.40 |
| h | $-C(CH_3)_2-O-\text{(C}_6\text{H}_{11})$ | 0.48 |

EXAMPLE 19a 6,9-Dioxo-11,15-bistetrahydropyranyloxy-(E)-2,(E)-13-prostadienoic acid methyl ester (XVI)

300 mg of 1[4(1-formyl-2-oxo)-butyl]-2-[3-tetrahydropyranyloxy-1-octenyl]-3-(tetrahydropyranyloxy)-5-oxo-cyclopentane (XV) and 570 mg of carbomethoxymethylenetriphenyl-phosphorane (loc.cit) in 20 ml of absolute toluene was stirred under N$_2$. The mixture was concentrated and the residue was purified in a silica gel column using ethyl acetate as eluant.

Yield: 232 g of yellow oil
$R_f$ 0.52 ethyl acetate

| NMR:δ | 7.2–6.6 | (m, 2H) |
|---|---|---|
| | 5.5–6.2 | (m, 2H) |
| | 4.9–4.5 | (m, 2H) |
| | 4.4–3.5 | (m, 4H) |
| | 3.8 | (s, 3H) |
| | 2.5 | (m, 7H) |
| | 2–0.8 | (m, 28 ) |

EXAMPLES 19b TO 19h

In the manner described in Example 19a the compounds according to Examples 18b to 18h could be converted by the Wittig reaction into the following compounds (formula XVI)

| EXAMPLE 19 | $R^2$ | $R_f$ values in ethyl acetate |
|---|---|---|
| b | $-CH_2-O-\text{(thiophene)}$ | 0.48 |
| c | $-CH_2-CH_2-\text{(thiophene)}$ | 0.44 |

-continued

| EXAMPLE 19 | R² | R_f values in ethyl acetate |
|---|---|---|
| d | CH₃\ ,,,CH₃ <br> –C–CH₂–O–CH₂–CH₃ | 0.59 |
| e | CH₃\ ,,,CH₃ <br> –C–CH₂–O–CH₃ | 0.51 |
| f | CH₃\ ,,,CH₃ <br> –C–CH₂–O–CH₂–CH₂–CH₃ | 0.52 |
| g | F <br> \| <br> –CH–CH₂–CH₂–CH₂–CH₃ | 0.46 |
| h | CH₃\ ,,,CH₃ <br> –C–O–⟨H⟩ | 0.54 |

EXAMPLE 20a

1[4(1-Formyl-3-oxo)-butyl]-2(3-hydroxy-1-octenyl)-3-hydroxy-cyclopentane-5-one (X)

280 mg of 1[4(1-formyl-3-oxo)-butyl]-2(3-tetrahydropyranyloxy-1-octenyl)-3-(tetrahydropyranyloxy)-5-oxo-cyclopentane (IX) (Example 17), 5 ml of dimethyl glycol, 5 ml of water and 1 ml of saturated oxalic acid solution were stirred for 13 hours at 50° C. The mixture was cooled, 10 ml of saturated sodium chloride solution were added, and the whole was saturated with NaCl and extracted with ethyl acetate. The organic phase was washed once with saturated NaCl/bicarbonate solution, dried over MgSO₄ and concentrated under reduced pressure. The impurities were removed over a silica gel column, first with ether/ethyl acetate 1:1 and then with ethyl acetate/glacial acetic acid 99:1 as an eluant.

Yield: 170 mg of colorless oil

Thin layer chromatogram (ethyl acetate/glacial acetic acid 97.5:2.5) on silica gel plates of Messrs. Merck R_f=0.55

EXAMPLES 20b to 20h:

In the manner described in Example 20a the compounds according to Examples 18b to 18h could be converted into the following compounds (formula IX) by splitting off the protective groups.

| EXAMPLE 20 | R² | R_f values |
|---|---|---|
| b | –CH₂–O–⟨S⟩ | 0.51 |
| c | –CH₂–CH₂–⟨S⟩ | 0.47 |
| d | CH₃\ ,,,CH₃ <br> –C–CH₂–O–CH₂–CH₃ | 0.60 |
| e | CH₃\ ,,,CH₃ <br> –C–CH₂–O–CH₃ | 0.57 |
| f | CH₃\ ,,,CH₃ <br> –C–CH₂–O–CH₂–CH₂–CH₃ | 0.56 |
| g | F <br> \| <br> –CH–CH₂–CH₂–CH₂–CH₃ | 0.52 |
| h | CH₃\ ,,,CH₃ <br> –C–O–⟨H⟩ | 0.55 |

EXAMPLE 21a:

6.9-Dioxo-11,15-dihydroxy-(E)-2, (E)-13-prostadienoic acid methyl ester (X)

168 mg of 6,9-dioxo-11,15-bistetrahydro-pyranyloxy-(E)-2, (E)-13-prostadienoic acid methyl ester (XVI), 5 ml of dimethyl glycol, 5 ml of water and 1 ml of saturated oxalic acid solution were stirred for 13 hours at 50° C. The mixture was cooled, 10 ml of saturated sodium chloride solution were added, and the whole was saturated with NaCl and extracted with ethyl acetate. The organic phase was washed once with saturated NaCl/bicarbonate solution, dried over MgSO₄ and concentrated under reduced pressure. The reaction product was freed from impurities over a silica gel column using first ether/ethyl acetate 1:1 and then ethyl acetate as an eluant.

Yield: 109 mg of light yellow oil; 2 isomers

R_f value 0.5 (ethyl acetate:glacial acetic acid 97.5:2.5); 0.45

| NMR: | 0.8–2.5 | (m, 21) | –CH₂, –CH |
|---|---|---|---|
|  | 3.0–3.5 | (m, 2) | –OH, |
|  | 3.5–4.4 | (m, 2) | –CH–OH |
|  | 3.8 | (s, 3) | –OCH₃ |
|  | 5.5–6.2 | (m, 2) | olefinic protons |
|  | 6.6–7.2 | (m, 2) | olefinic protons) |

EXAMPLES 21b to 21h:

In the manner described in Example 21a the protective groups could be detached from the compounds of the Examples 19b to 19h whereby the corresponding compounds of the formula X were obtained.

EXAMPLE 22a:

6,9,11,15-Tetrahydroxy-(E)-2, (E)-13-prostadienoic acid methyl ester (VII)

100 mg of 6,9-dioxo-11,15-dihydroxy-(E)-2, (E)-13-prostadienoic acid methyl ester (X) were dissolved in 30 ml of methanol and 2 ml of water and 2 g of sodium borohydride were added at 0° to 5° C. The mixture was stirred for 2 hours and the excess amount of sodium borohydride was decomposed with acetic acid. 20 ml of saturated NaCl solution were added and the mixture was extracted 4 times with 30 ml portions of chloroform, dried over MgSO₄ and concentrated under reduced pressure. The residue was filtered over a silica gel column using ethyl acetate as an eluant.

Yield: 90 mg of light yellow oil; 2 isomers (ethyl acetate/glacial acetic acid 9:1)

R_f=0.26 (ethyl acetate/glacial acetic acid=9:1); =0.22

| NMR: | 7.1–6.6 | (m, 2H) | olefinic protons |
|---|---|---|---|
|  | 6.1–5.4 | (m, 2H) | olefinic protons |
|  | 3.7 | (s, 3H) | OCH₃ |
|  | 4.4–3.5 | (m, 4H) | –CH–OH |
|  | 2.6–3.2 | (m, 4H) | OH |

-continued

| | | |
|---|---|---|
| 2.5-0.8 | (m, 21H) | —CH$_2$—, —CH— |

EXAMPLES 22b to 22h:

In the manner described in Example 22a the compounds according to Examples 9b to 9h could be reduced to give the following compounds (formula I, $X^1$, $Y^1$, $X^2$, $Y^2$ = hydrogen or hydroxyl, $X^1$ and $Y^1$, $X^2$ and $Y^2$ being different).

| EXAMPLE 22 | $R^2$ |
|---|---|
| b | —CH$_2$—O—[thienyl-S] |
| c | —CH$_2$—CH$_2$—[thienyl-S] |
| d | (CH$_3$)(CH$_3$)C—CH$_2$—O—CH$_2$—CH$_3$ |
| e | (CH$_3$)(CH$_3$)C—CH$_2$—O—CH$_3$ |
| f | (CH$_3$)(CH$_3$)C—CH$_2$—O—CH$_2$—CH$_2$—CH$_3$ |
| g | —CHF—CH$_2$—CH$_2$—CH$_2$—CH$_3$ |
| h | (CH$_3$)(CH$_3$)C—O—[cyclohexyl-H] |

What is claimed is:

1. A compound of the formula

[structure showing cyclopentane with $X^1$, $Y^1$ substituents, COOR$^1$ chain, OR$^3$, and R$^2$/OR$^3$ groups]

wherein:

$X^1$ and $Y^1$ taken alone are different and are hydrogen or hydroxy, or taken together are oxygen;

$R^1$ is
  (a) hydrogen or linear or branched, saturated or unsaturated, aliphatic or cycloaliphatic hydrocarbon having up to 10 carbon atoms, or is
  (b) a physiologically acceptable metal ion, an NH$_4^+$ ion, or an ammonium ion derived from a primary, secondary, or tertiary amine;

$R^2$ is linear or branched alkyl having 1 to 7 carbon atoms substituted with
  (a) α- or β-thienyl or furyl, which thienyl or furyl in turn may be mono-, di-, or tri-substituted in the nucleus with at least one member selected from the group consisting of halogen, trifluoromethyl, alkyl having 1 to 6 carbon atoms, and alkoxy having 1 to 6 carbon atoms, or
  (b) α- or β-thienyloxy or such thienyloxy mono-, di-, or tri-substituted in the nucleus with at least one member selected from the group consisting of halogen, trifluoromethyl, alkyl having 1 to 6 carbon atoms, and alkoxy having 1 to 6 carbon atoms; and $R^3$ is hydrogen, 1-ethoxyethyl, tetrahydropyran-2-yl, or tetrahydrofuran-2-yl, or is such tetrahydropyranyl or tetrahydrofuranyl mono- or poly-substituted by alkyl.

2. A compound as in claim 1 wherein $X^1$ and $Y^1$ are taken together and are oxygen and wherein $R^3$ is hydrogen.

3. A compound as in claim 1 which is 6,9-dioxo-11,15-dihydroxy-16-(3-thienyloxy)-17,18,19,20-tetranor-(E)-2,(E)-13-prostadienoic acid.

4. A compound as in claim 1 which is 6,9-dioxo-11,15-dihydroxy-17-(3-thienyloxy)-18,19,20-tetranor-(E)-2,(E)-13 prostadienoic acid.

5. A pharmaceutical composition useful for treating hypertonia or inhibiting blood platelet aggregation comprising a therapeutically-effective amount of a compound as in claim 1 together with a pharmaceutically acceptable carrier therefor.

6. A method for treating hypertonia in a patient suffering therefrom which comprises administering to said patient an anti-hypertensively effective amount of a compound as in claim 1.

7. A method for inhibiting blood platelet aggregation in a patient in need of such treatment which comprises administering to said patient an amount, effective to inhibit blood platelet aggregation, of a compound as in claim 1.

* * * * *